United States Patent [19]

Sanderson et al.

[11] Patent Number: 4,483,998

[45] Date of Patent: Nov. 20, 1984

[54] SIMULTANEOUS EPOXIDE AND CARBOXYLIC ACID MANUFACTURE BY CO-OXIDATION IN THE PRESENCE OF A COPPER-BORON-SILVER CATALYST

[75] Inventors: John R. Sanderson; Edward T. Marquis, both of Austin; Jiang-Jen Lin, Round Rock, all of Tex.

[73] Assignee: Texaco Inc., White Plains, N.Y.

[21] Appl. No.: 484,058

[22] Filed: Apr. 11, 1983

[51] Int. Cl.$^3$ ............................................ C07D 301/06
[52] U.S. Cl. .................................................. 549/533
[58] Field of Search ........................................ 549/533

[56] References Cited

U.S. PATENT DOCUMENTS

| | | | |
|---|---|---|---|
| 3,347,763 | 10/1967 | Coffey et al. | 549/533 |
| 3,716,562 | 2/1973 | Pregaglia et al. | 549/533 |
| 3,821,259 | 6/1974 | Bljumberg et al. | 549/533 |
| 4,046,783 | 9/1977 | Cavitt | 549/533 |
| 4,256,650 | 3/1981 | Bljumberg et al. | 549/533 |
| 4,390,738 | 6/1983 | Waddan et al. | 549/533 |

FOREIGN PATENT DOCUMENTS 11847 6/1966 Japan .

*Primary Examiner*—Norma S. Milestone
*Attorney, Agent, or Firm*—Jack H. Park; Kenneth R. Priem; David L. Mossman

[57] ABSTRACT

A process for simultaneously producing an epoxide and a carboxylic acid from an olefin and an aldehyde, respectively, by co-oxidation over a catalyst in the presence of oxygen is described. The catalyst is made by precipitating silver oxide in the presence of copper(II) oxide, copper(II) borate or a mixture thereof. These novel heterogeneous catalysts provide higher selectivities to the epoxide than those obtainable with commercial catalysts.

6 Claims, No Drawings

SIMULTANEOUS EPOXIDE AND CARBOXYLIC ACID MANUFACTURE BY CO-OXIDATION IN THE PRESENCE OF A COPPER-BORON-SILVER CATALYST

BACKGROUND OF THE INVENTION

1. Field of the Invention

The invention relates to oxidation reactions in which epoxides are produced, and particularly relates to catalytic co-oxidations where an epoxide and a carboxylic acid are simultaneously produced from an olefin and an aldehyde, respectively.

2. Other Related Methods in the Field

It is known in the art to produce olefin oxides, especially ethylene oxide by reaction of the olefin in the vapor phase in the presence of silver catalysts. Various improvements have been made in this process including catalysts, reaction conditions and reactor design.

The direct oxidation of propylene to propylene oxide in the presence of silver catalysts is also known but the selectivity is low (50% at best), see Stanford Research Institute Report 2C, p. 259.

The direct liquid phase noncatalytic oxidation of propylene is also known in the art. The noncatalytic process results in low selectivity to the desired propylene oxide and a large number of co-products.

It is also known to oxidize propylene to propylene oxide in the presence of a catalyst. A high yield of epoxide is claimed using silica containing oxides of scandium, etc. as the catalyst (German Pat. No. 2,313,023). In this example, however, acetone is used as solvent and under these conditions acetone is consumed along with propylene.

U.S. Pat. No. 2,985,668 concerns the reaction of unsaturated compounds (including propylene) in the liquid phase (using high boiling solvents) in the presence of finely divided silver catalysts which were suspended in the liquid. Solvents claimed were mainly high boiling esters of carboxylic acids.

Most of the work concerning the silver catalyzed oxidation of olefins has been with ethylene and it is known that additives such as ethylene dichloride (EDC) and other chlorinated hydrocarbons retard the formation of by-products, see U.S. Pat. Nos. 2,279,469 and 2,734,906.

Co-oxidation procedures are also well known in the art. For example, the noncatalytic epoxidation of olefins by co-oxidation with secondary aliphatic aldehydes which are converted to the corresponding acids is taught by U.S. Pat. No. 3,265,716. The co-oxidation of propylene and p-tolualdehyde where water is used as a solvent is known, propylene glycol and p-toluic acid being the main products.

The kinetics and mechanics of the coupled oxidation of propylene and acetaldehyde are discussed in *Bull. Acad. Sci.* (USSR), vol. 8 (1966), p. 1283. The co-oxidation of benzaldehyde and cyclohexene in the presence of metal complexes containing platinum, rhodium, manganese, cobalt or molybdenum is described in another Russian article, see *Chemical Abstracts* 91:55955z (1979).

It is also known that propylene oxide and propylene glycol can be simultaneously produced by the oxidation of propylene over cobalt acetate according to Japanese Patent 80-021021. p-Tolualdehyde is also present, serving as a promoter, though it is also oxidized to the corresponding peracid.

The gas phase oxidation of acetaldehyde and propylene mixtures is reported as being an uneconomical process for the production of propylene oxide in *Kogyo Kagaku Zasshi*, vol. 69 (1966), p. 1863.

Methods for producing the acids alone are also known. For example, Japanese Patent 72-22,569 reveals that peroxy acids may be prepared by bubbling air into a solution of a benzaldehyde using a metal oxide such as mercury oxide, zinc oxide and cerium oxide as a catalyst. The preparation of carboxylic acids by oxidation of aldehydes with chloride is described in *Acta. Chim. Scand.*, vol. 17 (1973), p. 880. Cobalt acetate is known to catalyze the oxidation of benzaldehyde according to *Acta. Chim.* (Budapest), vol. 78 (1973), p. 193.

U.S. Pat. No. 4,338,462 discloses a process for oxidizing methacrolein to methacrylic acid salt in the presence of oxygen and a strongly alkaline medium over a finely divided silver catalyst.

Of course, epoxidation of olefins is well known. German Pat. No. 3,002,811 discloses the epoxidation of cyclododecene or tricyclododecene with performic acid being generated "in situ" from hydrogen peroxide and formic acid. Epoxide production from olefins and hydrogen peroxide in an anhydrous solvent containing a boron catalyst according to German Pat. No. 2,952,755.

There is still a need for oxidation processes which provide a high yield to the epoxide. Preferably, such methods would employ a heterogeneous catalyst system.

SUMMARY OF THE INVENTION

The invention concerns a process for simultaneously producing an epoxide and a carboxylic acid comprising passing oxygen through a mixture of an olefin and an aldehyde in the presence of a catalyst system containing copper, boron and silver. The olefin has the formula R—CH=CH—R', where R is an alkyl group of from one to twenty carbon atoms and R' is hydrogen or an alkyl group of from one to nineteen carbon atoms and where R and R' are linked together, the olefin is a cycloalkene. The aldehyde has the formula R"—CHO where R" is an alkyl or aromatic group of one to twelve carbon atoms.

DETAILED DESCRIPTION OF THE PREFERRED EMBODIMENTS

The inventive method produces carboxylic acids and epoxides simultaneously. Carboxylic acids are well known as useful compounds. The epoxides (alkylene oxides) are of interest in the manufacture of important, high volume products, including urethane polyols, alkylene glycols, surfactants and detergents, alkanolamines, fumigants, synthetic lubricants, gasoline additives and elastomers.

According to the method of this invention, the olefin (alkene) feedstocks may consist of any mono olefin having the double bond located anywhere within the molecule and, possibly, mixtures of such olefins. The olefin may be an alpha or an internal olefin. These olefins may be represented by the structure R—CH=CH—R', where R is an alkyl group of from one to twenty carbon atoms and R' is hydrogen or an alkyl group of from one to nineteen carbon atoms. Both R and R' can be linked together to form a cyclic olefin or cycloalkene. Specific examples of suitable olefins include, but are not limited by, the following list: propylene, 1-butene, 2-butene, 1-pentene, 2-pentene, 1-hexene, 2-hexene, 3-hexene, cyclohexene, heptenes, octenes, nonenes, decenes, cyclodecenes, undecenes, dodecenes, cyclododecenes, tridecenes, etc., and mixtures thereof.

The aldehyde may be any molecule with a —CHO group, preferably an aliphatic or aromatic aldehyde. These aldehydes may be represented by the structure R″—CHO, where R″ is an alkyl or aromatic group of one to twelve carbon atoms. Specific examples of suitable aldehydes include, but are not limited by, the following list: acetaldehyde, propionaldehyde, butyraldehyde, heptaldehyde, benzaldehyde, etc. The proportion of olefin to aldehyde should range from about 0.1:1.0 to 1.0:0.1, preferably from about 1.0:1.0 to 1.0:0.5. This proportion should be allowed to change with economics, as it is not dependent so much on the technology.

Of course, molecular oxygen in a pure form or air is an essential co-reactant for the method of this invention. The reaction is run liquid phase with the oxygen or air being pumped through the liquid; the catalyst being a heterogeneous solid.

The solvents used must be compounds that are inert with respect to the oxidation reaction. These compounds may be generally described as non-polar, aromatic organic solvents. Suitable solvents are halobenzenes and alkylbenzenes. Specifically preferred solvents are chlorobenzene and dibutyl phthalate.

Catalysts found to be useful in the method of this invention are those formed by precipitating silver oxide in the presence of copper oxides, copper borates and mixtures thereof. It is preferred that the catalyst system contain copper, boron and silver. It is especially preferred that the catalyst is a mixture of copper(II) oxide, copper(II) borate and silver oxide.

The reaction conditions under which the method of this invention may be conducted include a temperature range of from 50° to 150° C. A preferred range is from 50° to 90° C. The pressure may be one atmosphere or higher. Due to the use of the Cu-B-Ag catalysts of this invention, these conditions are much milder than many of those in the prior art discussed earlier.

Although the resultant proportion of carboxylic acid product is not analyzed for, it is known to be present. It was identified in previous work on a very similar reaction (co-oxidation using benzaldehyde). An aqueous bicarbonate extract of the reaction mixture was acidified with dilute hydrochloric acid to a pH of about 2. The white solid was collected with suction, washed with a little water and air dried. The solid was identified as benzoic acid by its melting point (121°–122° C.).

The invention will be further illustrated by the following examples which are not intended to limit the scope of the invention.

EXAMPLE I

Preparation of $CuO.Cu(BO_2)_2.Ag_2O$ Catalyst

Copper(II) oxide (90 g) and copper(II) borate (10 g) were slurried in 200 ml of de-mineralized water containing 5 g of NaOH. Silver nitrate (20 g) was dissolved in 100 ml of de-mineralized water and added dropwise to the above slurry while stirring vigorously. The mixture was stirred for 30–45 minutes and the solid filtered with suction and washed well with water. The solid (after drying at about 130° C. for three days) weighed 110 g. The solid contained 10.6% Ag by atomic absorption analysis.

EXAMPLE II

Preparation of $Cu(BO_2)_2.Ag_2O$ Catalyst

Copper(II) borate (9.5 g) was slurried in 25 ml of de-mineralized water containing 0.5 g of NaOH. Silver nitrate (0.5 g) dissolved in 10 ml of demineralized water was added slowly to the slurry which was vigorously stirred. The mixture was stirred for 35–45 minutes, the solid filtered with suction and washed with water. The solid (after drying at about 130° C. for three days) weight 10 g and contained 3.88% Ag (by atomic absorption analysis).

Other Salts

The other salts used were commercial materials.

EXAMPLES III–XXIX

Procedure for Simultaneously Making Epoxide and Carboxylic Acid

A small resin flask was fitted with a condenser, mechanical stirrer, fritted glass addition tube and thermometer. Chlorobenzene (50 ml), reactants, and catalyst were charged to the flask and the mixture heated to the desired temperature. Air was bubbled through the stirred reaction mixture at 50 ml/min. for the time indicated. The temperature was maintained at ±2° C. by means of a Therm-O-Watch temperature regulator. At the end of the reaction, the mixtures were poured into an equal volume of water. The aqueous layer was drawn off and discarded and the organic layer washed twice with an equal volume of dilute bicarbonate, once with water, and once with saturated sodium chloride. The solution was dried over anhydrous sodium sulfate and analyzed by vapor phase chromatography. The results are shown in Table I.

TABLE I

| | CO-OXIDATION OF 1-DODECENE AND BENZALDEHYDE IN CHLOROBENZENE | | | | | | | |
|---|---|---|---|---|---|---|---|---|
| Example | 1-Dodecene (Mol) | Benzaldehyde (Mol) | Catalyst | g | Temp. (°C.) | Time (Hr) | 1-Dodecene Conv. (A %) | Epoxide Select. (A %) |
| III | 0.10 | 0.05 | None | — | 80 | 19 | 7.7 | 34.0 |
| IV | 0.10 | 0.05 | None | — | 80 | 19.5 | ~0 | — |
| V | 0.10 | 0.05 | None | — | 80 | 20 | <1 | — |
| VI | 0.10 | 0.05 | None | — | 80 | 22.5 | ~0 | — |
| VII | 0.05 | 0.05 | $Cu(OAc)_2$ | 0.01 | 80 | 18 | 62.5 | 79.0 |
| VIII | 0.05 | 0.05 | $Co(OAc)_2$ | 0.01 | 80 | 19 | 59.7 | 72.0 |
| IX | 0.05 | 0.05 | $Ni(OAc)_2$ | 0.01 | 80 | 20 | 2.9 | 24.1 |
| X | 0.05 | 0.05 | $Cu(OAc)_2$ | 0.01 | 80 | 20 | 57.2 | 66.3 |
| XI | 0.05 | 0.05 | $Co(OAc)_2$ | 0.01 | 80 | 20 | 58.0 | 59.5 |
| XII | 0.05 | 0.05 | $Mn(OAc)_2$ | 0.01 | 80 | 20 | <1 | — |
| XIII | 0.05 | 0.05 | $CuO.Cu(BO_2)_2.Ag_2O$ | 0.01 | 80 | 19 | 65.5 | 86.6 |
| XIV | 0.10 | 0.05 | $CuO.Cu(BO_2)_2.Ag_2O$ | 0.01 | 80 | 20 | 29.4 | 85.7 |
| XV | 0.10 | 0.05 | $CuO.Cu(BO_2)_2.Ag_2O$ | 0.05 | 80 | 20.5 | 30.8 | 82.1 |

TABLE I-continued

CO-OXIDATION OF 1-DODECENE AND BENZALDEHYDE IN CHLOROBENZENE

| Example | 1-Dodecene (Mol) | Benzaldehyde (Mol) | Catalyst | g | Temp. (°C.) | Time (Hr) | 1-Dodecene Conv. (A %) | Epoxide Select. (A %) |
|---|---|---|---|---|---|---|---|---|
| XVI | 0.10 | 0.05 | $CuO.Cu(BO_2)_2.Ag_2O$ | 0.05 | 80 | 5 | 16.3 | 79.8 |
| XVII | 0.10 | 0.05 | $CuO.Cu(BO_2)_2.Ag_2O$ | 0.01 | 70 | 20.5 | 9.7 | 79.2 |
| XVIII | 0.10 | 0.05 | $Cu(BO_2)_2.Ag_2O$ | 0.01 | 80 | 20.5 | ~0 | — |
| XIX | 0.10 | 0.05 | $CuO.Cu(BO_2)_2.Ag_2O$ | 0.01 | 60 | 21 | 8.3 | 82.8 |
| XX | 0.10 | 0.05 | $Cu(BO_2)_2.Ag_2O$ | 0.01 | 80 | 21 | 50.5 | 79.0 |
| XXI | 0.10 | 0.05 | $CuO.Cu(BO_2)_2.Ag_2O$ | 0.10 | 80 | 20.5 | 36.7 | 82.3 |
| XXII | 0.10 | 0.05 | $Cu(BO_2)_2.Ag_2O$ | 0.01 | 70 | 20.5 | 39.7 | 82.9 |
| XXIII | 0.10 | 0.05 | $Cu(BO_2)_2.Ag_2O$ | 0.01 | 60 | 22 | 25.2 | 81.7 |
| XXIV | 0.01 | 0.05 | $Cu(BO_2)_2.Ag_2O$ | 0.005 | 80 | 5 | ~0 | — |
| XXV | 0.10 | 0.05 | CuO $Cu(BO_2)_2$ | 0.005 0.005 | 80 | 21.5 | 39.2 | 78.8 |
| XXVI | 0.10 | 0.05 | CuO $Cu(BO_2)_2$ | 0.01 0.001 | 80 | 21.5 | ~0 | — |
| XXVII | 0.10 | 0.05 | CuO $Cu(BO_2)_2$ $Ag_2O$ | 0.01 0.005 0.005 | 80 | 21 | 32.8 | 89.0 |
| XXVIII | 0.10 | 0.05 | $Ag_2O$ | 0.01 | 80 | 21 | 48.6 | 75.5 |
| XXIX | 0.10 | 0.05 | $Ag_2O$ | 0.10 | 80 | 6 | 12.3 | 62.3 |

With respect to Table I, it may be seen that Examples III through VI give both low conversions of the 1-dodecene reactant and poor selectivities to the epoxide. Conversions should be at least 8 area % or larger and epoxide selectivities should be around 80 area % or larger. The criteria are met by the most preferred catalyst, a combination of copper(II) oxide, copper(II) borate and silver oxide whether in a co-precipitated complex (Examples XIII through XVII, XIX and XXI) or whether mixed separately (Example XXVII). The examples using a copper borate/silver oxide catalyst (Examples XVIII, XX, XXII, XXIII and XIV) were also good except for Example XXIV where the catalyst portion was probably too low, and Example XVIII, for unknown reasons. Examples using copper, cobalt, nickel and manganese acetates are presented for comparison (Examples VII-XII). Other comparative examples using copper oxide/copper borate combinations or only silver oxide as the catalysts are also presented (Examples XXV, XXVI, XVIII and XXIX) and show that the selectivities to the oxide are not as great as when the especially preferred Cu-B-Ag combination is used.

EXAMPLE XXX

Cyclododecene Oxidation

The procedure was the same as for Examples III through XXIX above except that 0.05 mole of cyclododecene and 0.05 moles of benzaldehyde were oxidized at 80° C. in the presence of 0.01 g of $Cu(BO_2)_2.Ag_2O$ for 21 hours. A 9.5% conversion was obtained with 95 area % selectivity to the epoxide.

Many modifications may be made in this invention by those skilled in the art without departing from the spirit and scope of the invention which are defined in the appended claims. For example, a particular catalyst proportion combination, olefin/aldehyde combination or mode of reaction or addition could prove to be particularly advantageous.

We claim:

1. A process for simultaneously producing an epoxide and a carboxylic acid comprising passing oxygen through a mixture of an olefin of the formula R—CH=CH—R', where R is an alkyl group from one to twenty carbon atoms and R' is hydrogen or an alkyl group of from one to nineteen carbon atoms and where R and R' are linked together, the olefin is a cycloalkene, and an aldehyde of the formula R"—CHO, where R" is an alkyl or aromatic group of one to twelve carbon atoms, in the liquid phase, in the presence of a catalyst system produced by precipitating silver oxide in the presence of copper(II) borate or a mixture of copper(II) oxide and copper(II) borate, and in the presence of an organic, inert solvent.

2. The process of claim 1 in which the proportion of olefin to aldehyde ranges from 0.1:1.0 to 1.0:0.1.

3. The process of claim 1 in which the reaction is conducted at a temperature between about 50° and 150° C.

4. The process of claim 1 in which the catalyst system is produced by precipitating silver oxide in the presence of a mixture of copper(II) oxide and copper(II) borate.

5. The process of claim 1 in which the olefin is 1-dodecene and the aldehyde is benzaldehyde.

6. The process of claim 1 in which the inert solvent is chlorobenzene.

* * * * *